United States Patent
Cha

Patent Number: 6,090,049
Date of Patent: Jul. 18, 2000

[54] SCREEN-TYPE SPIROMETER HAVING AN IMPROVED PNEUMOTACHOMETER

[76] Inventor: Eun Jong Cha, 208-205, Jugong 2 Apt., Mochung-Dong, Hungduck-Ku, Cheongju-City, Rep. of Korea

[21] Appl. No.: 09/122,140

[22] Filed: Jul. 24, 1998

[30] Foreign Application Priority Data

Mar. 4, 1998 [KR] Rep. of Korea ............... 98-7078

[51] Int. Cl.⁷ .................................................. A61B 5/08
[52] U.S. Cl. ........................................................ 600/538
[58] Field of Search .................................. 600/532, 538, 600/529, 533; 73/23.3, 861.42, 861.53

[56] References Cited

U.S. PATENT DOCUMENTS

| | | | |
|---|---|---|---|
| 4,989,456 | 2/1991 | Stupecky | 600/538 |
| 5,033,312 | 7/1991 | Stupecky | 600/538 |
| 5,038,621 | 8/1991 | Stupecky | 600/538 |
| 5,060,655 | 10/1991 | Rudolph | 600/532 |
| 5,107,860 | 4/1992 | Malouvier et al. | 600/533 |
| 5,111,827 | 5/1992 | Rantala | 600/532 |
| 5,462,061 | 10/1995 | Malouvier et al. | 600/533 |
| 5,522,397 | 6/1996 | Vermaak | 600/533 |
| 5,564,432 | 10/1996 | Thomson | 600/533 |

*Primary Examiner*—Cary O'Connor
*Assistant Examiner*—Navin Natnithithadha
*Attorney, Agent, or Firm*—Omri M. Behr, Esq.

[57] ABSTRACT

Disclosed is a screen-type spirometer having an improved pneumotachometer, which has a simple structure and a low manufacturing cost and is convenient to use. According to the present invention, the pneumotachometer includes a hollow housing having an annularly shaped ring and a first respiratory tube integrally formed with the annularly shaped ring. The first respiratory tube can be inserted into a mouth of a person to be examined. The pneumotachometer also includes a second respiratory tube which can be engaged with the housing and be inserted into the mouth of the person. The first and the second respiratory tubes have a tapered portion, which is inclined at 10 degrees, respectively in order to stabilize a fluid flow of respiratory gases passing therethrough. O-shaped first and second sensing units for sensing a differential pressure of the respiratory gases passing through the pneumotachometer are disposed within the housing. A circularly shaped screen operating as a mechanical resistance against the respiratory gases is disposed between the first sensing unit and the second sensing unit within the housing. Preperably, a suitable size for the screen has been found to be in the range of a screen having a mesh of 300 openings per inch. The pneumotachometer comprises a blowing apparatus for drying and cleaning the screen at need. The blowing apparatus is provided as an individual unit. A handle is attached to an outer surface of the annularly shaped ring.

17 Claims, 6 Drawing Sheets

SCREEN-TYPE SPIROMETER HAVING AN IMPROVED PNEUMOTACHOMETER

BACKGROUND OF THE INVENTION

1. Field of the Invention

The present invention relates to a screen-type spirometer having an improved pneumotachometer, which has a simple structure and a low manufacturing cost and is convenient to use.

2. Description of the Related Art

Generally, an examination of the capacity of the lungs is a kind of a synthetic lungs function examination, and is used in evaluating all of ventilatory functions and a part of distributive functions among functions of the lungs. In other words, the examination of the capacity of the lungs is a widely-used examination which commands an overwhelming majority in examining the functions of the lungs. The examination of the capacity of the lungs mainly evaluating the ventilatory functions can be applied to examine a respiratory function of a patient having a specific disease or a patient to be undergone an operation. Further, the examination of the capacity of the lungs can be applied to diagnose a health condition of a general person or a sufferer from an industrial disease, etc. At the present time, due to the industrialization, the environmental pollution is growing more and more serious and thereby the number of the sufferer from the industrial disease is rapidly increased. At this point of time, the examination of the capacity of the lungs is regarded as a very important examination.

Generally speaking, two types of pneumotach apparatus have been used in examining the capacity of the lungs. One type of the pneumotach apparatus is an apparatus for quantitatively measuring the capability of lung volume, which is an expansion and a contraction of the lungs. This apparatus directly measures the change of the lung volume while a person to be examined breathes according to a breathing protocol which is arranged beforehand. The other type of the pneumotach apparatus is an apparatus for sensing a fluid flow passing through the lungs inward or outward while the person breathes and for determining the quantity of respiration of the person by integrating the flow measurement values.

In the past, the former apparatus had been mainly used in examining the capacity of the lungs. However, the structure of the former apparatus is relatively complicated and the dynamic response thereof is not satisfactory. Accordingly, at the present time, the latter apparatus has been widely used in examining the capacity of the lungs.

Various types of the latter apparatus have been used for measuring a volume flow of the fluid flow per unit time. The respiratory gas streams at a great volume, and the latter apparatus must continuously measure an absolute quantity of the gas flow flowing in both directions(inspiratory and expiratory) and must provide a relatively accurate flow measurement to an operator thereof regardless of the change of measuring environment. Further, in the use of the latter apparatus, this apparatus must not hinder the respiration of the patient. Therefore, a measuring method of the latter apparatus is limited. Since the latter apparatus must continuously measure the absolute quantity of the fluid flow, it must employ a measuring method indicating an excellent dynamic response.

Pneumotachography, which has been widely used in research and development for respiratory organs, can be employed as the measuring method capable of satisfying the conditions described above. Pneumotachography uses a phenomenon that fluid energy of the respiratory gases is lost due to the friction generated between the fluid flow and a screen acting as a mechanical resistance at the time that the respiratory gases pass through the screen thereby a pressure drop of the fluid flow corresponding to the lost fluid energy is generated. At this time, the pressure drop is associated with the respiratory gas flow. Accordingly, it is possible to calculate a quantity and the flow direction of the respiratory gases by measuring a variance in a respiratory pressure difference on both sides of the screen.

U.S. Pat. No. 5,060,655, issued to Kelvin A. Rudolph on Oct. 29, 1991, discloses a pneumotach apparatus having a pneumotachometer and subsidiary equipments used in conjunction with the pneumotachometer. This pneumotach apparatus uses the respiratory gases measuring manner as described above. In this pneumotach apparatus, the pneumotachmeter includes a passageway and having a plurality of screens disposed within the passageway. The subsidiary equipments of the pneumotach apparatus comprise a pressure transducer which is fluid-communicated with the pneumotachmeter by means of a pair of flexible tubes, and comprise a flow indicating instrument for displaying a flow measurement of the respiratory gases which is connected to the pressure transducer by means of a conduit.

Figure 5:
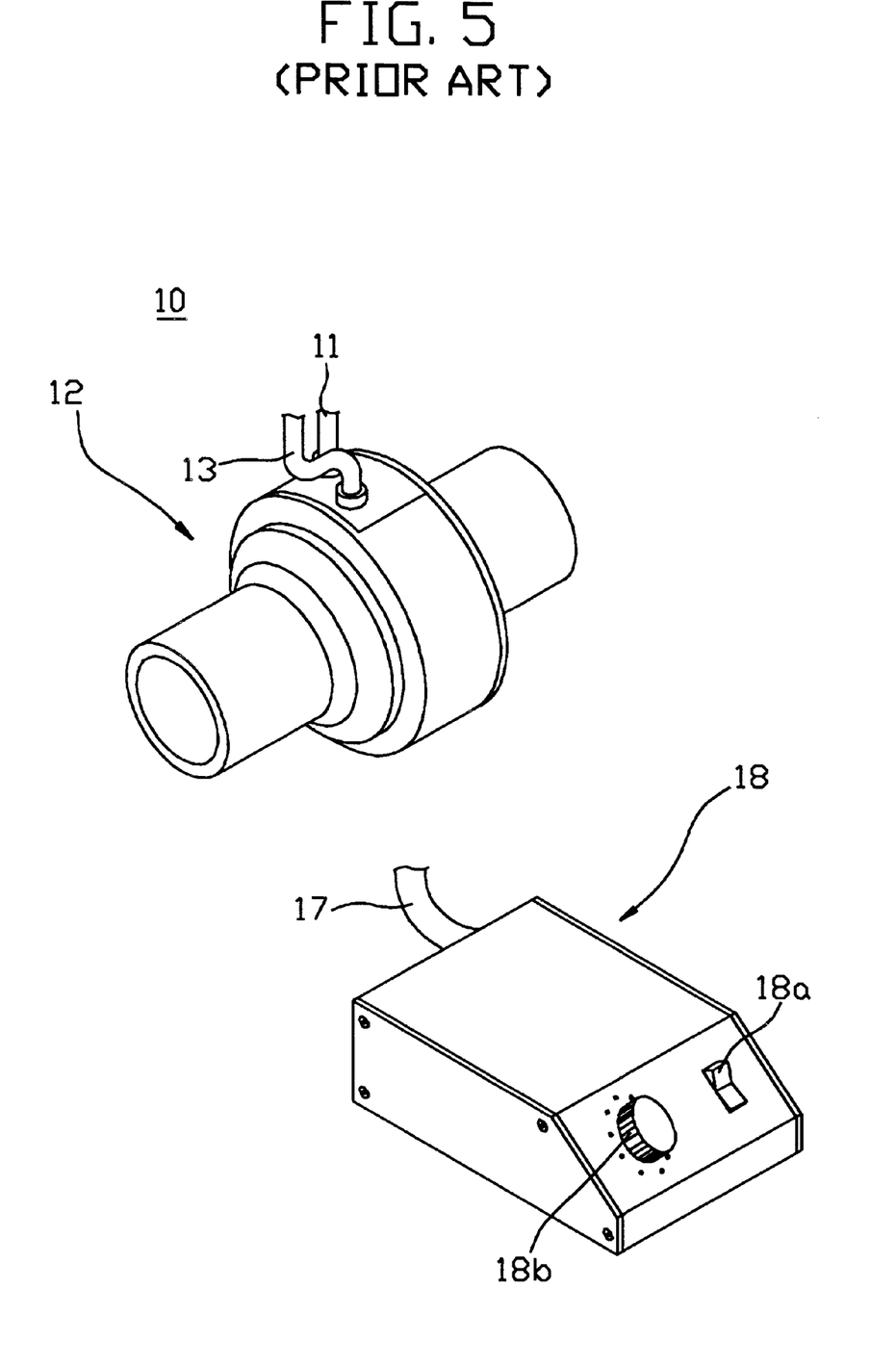
FIG. 5 illustrates schematically a screen-type spirometer according to a prior art, with subsidiary equipments of the spirometer omitted for the sake of clarity.

FIG. 5 illustrates schematically a screen-type spirometer according to a prior art, with subsidiary equipments of the spirometer omitted for the sake of clarity. Referring to FIG. 5, a pneumotach apparatus 10 mainly includes a pneumotachometer 12, a screen heater 18, a pressure transducer (not shown) and a flow indicating instrument (not shown). Pneumotachometer 12 is fluid-communicated with the pressure transducer by a pair of flexible tubes 11, 13. Screen heater 18 is electrically connected to pneumotachometer 12 by a cable 17. Screen heater 18 is used for heating a plurality of circularly shaped screens 60a,60b,60c(referred to FIG. 6), which are disposed within a passageway for allowing the respiratory gases to flow therethrough, in order to remove a humidity formed on screens 60a,60b,60c after using pneumotachometer 12. Screen heater 18 includes an on/off switch 18a and a screen temperature setting switch 18b.

Figure 6:
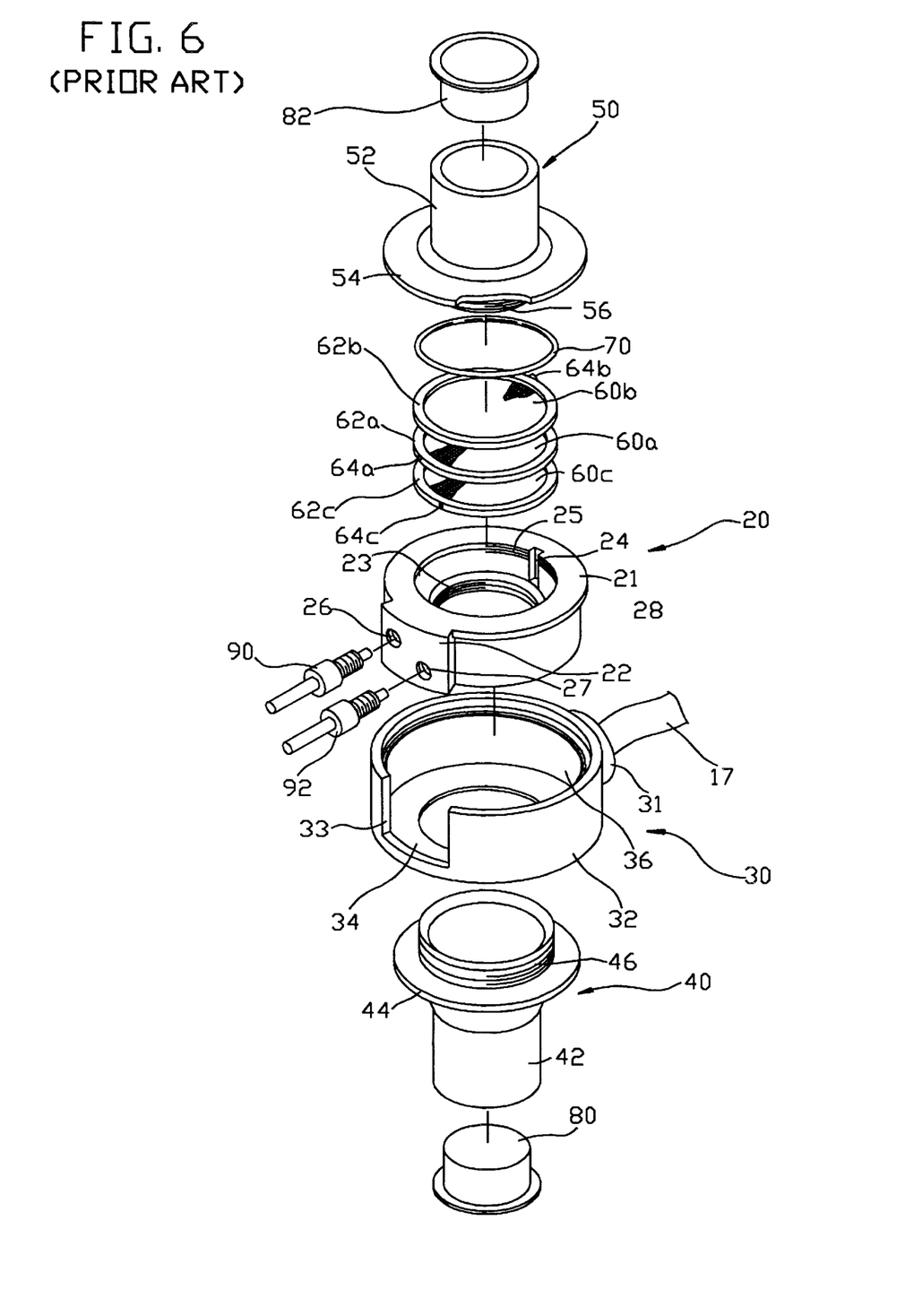
FIG. 6 is an enlarged and exploded perspective view of a pneumotachometer illustrated in FIG. 5.

FIG. 6 is an enlarged and exploded perspective view of a pneumotachometer illustrated in FIG. 5. Referring to FIG. 6, pneumotachometer 12 includes an annularly shaped first housing 20, an annularly shaped second housing 30, a hollow first tube adapter 40, a hollow second tube adapter 50, screens 60a,60b,60c, an annularly shaped sealing ring 70, a first cover 80 and a second cover 82, a first pressure tap 90 and a second pressure tap 92.

First housing 20 includes a shoulder 21 extending radially outward from an upper portion of first housing 20, a protrusion 22 extending radially outward from at an outer surface of first housing 20, a first female threaded portion 23 formed at an inner lower end of first housing 20 and a second female threaded portion 25 formed at an inner upper end of first housing 20.

Further, a locking groove 24 is vertically formed at an inner surface of first housing 20. A first through hole 26 and a second through hole 27 for receiving first pressure tap 90 and second pressure tap 92, respectively, are formed at protrusion 22 of first housing 20.

When pneumotachometer 12 is assembled at a one body, second housing 30 receives first housing 20. In order to accomplish this task, an annularly shaped second ring 32 of second housing 30 has an inner diameter greater than an outer diameter of an annularly shaped first ring 28 of first housing 20. Cable 17 extending from screen heater 18 (referred to FIG. 5) is connected to a cable connecting portion 31 provided on an outer surface of second housing 30. An aperture 33 is formed at a position of the other surface of second housing 30 which is opposite to cable connecting portion 31. When first housing 20 and second housing 30 are combined with each other, protrusion 22 of first housing 20 is fitted into aperture 33.

An annularly shaped locking portion 34 is formed at an inner lower portion of second housing 30. When first housing 20 and second housing 30 are combined with each other, locking portion 34 supports a bottom outer surface of first housing 20. A metal heating element 36 is installed on an inner surface of second housing 30. Heating element 36 heats screens 60a,60b,60c disposed within first housing 20 at need under the state that first housing 20 and second housing 30 are combined with each other. In other words, when an electric current is applied to heating element 36 from screen heater 18 through cable 17, heating element 36 heats screens 60a,60b,60c.

Screens 60a,60b,60c act as mechanical resistances and are made of stainless steel. A suitable size for screens 60b and 60c among them has been found to be in the range of a screen having a mesh between 100 and 130 openings per inch. On the contrary, a suitable size for main screen 60a has been found to be in the range of a screen having a mesh between 300 and 330 openings per inch. Main screen 60a acts as the substantial mechanical resistance, and screens 60b and 60c stabilize the fluid flow. Screens 60a,60b,60c have screen members 62a,62b,62c for supporting a netting loop of screens 60a,60b,60c, respectively. Locking projections 64a,64b,64c are formed on outer surfaces of main screen 60a and screens 60b,60c, respectively. When main screen 60a and screens 60b,60c are disposed within first housing 20, locking projections 64a,64b,64c are snugly fitted within locking groove 24 formed at the inner surface of first housing 20.

First tube adapter 40 is provided with a first hose receiving portion 42 and an annularly shaped first flange 44. First hose receiving portion 42 receives a hose(not shown) for transferring the respiratory gases which is conventionally used to measure the capacity of the lungs of a patient. First cover 80 can be fitted into a distal end of first hose receiving portion 42. When first tube adapter 40 is engaged with second housing 30, first flange 44 tightly contacts with a bottom outer surface of second housing 30. Meanwhile, a first male threaded portion 46 is formed at an upper end of first tube adapter 40. When first tube adapter 40 is engaged with second housing 30, first male threaded portion 46 is engaged with first female threaded portion 23 of first housing 20 which is fitted into second housing 30.

In the same manner as first tube adapter 40, second tube adapter 50 is provided with a second hose receiving portion 52 and an annularly shaped second flange 54. Second cover 82 can be inserted into a distal end of second hose receiving portion 52. When second tube adapter 50 is engaged with first housing 20, second flange 54 tightly contacts with an upper surface of shoulder 21 of first housing 30. Meanwhile, a second male threaded portion 56 is formed at a lower end of second tube adapter 50. When second tube adapter 50 is engaged with first housing 20, second male threaded portion 56 is engaged with second female threaded portion 25 which is formed at an upper end of the inner surface of first housing 20.

Since pneumotach apparatus 10 constructed as described above is provided with the high-priced screens 60a,60b,60c within pneumotachometer 12, there is a problem that the total manufacturing cost of pneumotach apparatus 10 is too expensive. Further, an internal structure of pneumotach apparatus 10 is relatively complicated and therefore the manufacturing process of pneumotach apparatus 10 is also complicated. In addition, when an inspector or a doctor uses screen heater 18 in order to remove the humidity formed on screens 60a,60b,60c of pneumotachometer 12 after using pneumotach apparatus 10 to a person to be examined, a next person to be examined must wait for a duration of time until the humidity formed on screens 60a,60b,60c are completely removed. Further, any dirts and microorganisms within the humid cannot be removed and can cause a secondary infection, by just heating and drying, to the next person to be examined. In other words, only humidity not dirts is removed by heating the pneumotachometer. Accordingly, it is inconvenient to use pneumotach apparatus 10.

SUMMARY OF THE INVENTION

The present invention is contrived to solve the foregoing problems. It is an object of the present invention to provide a screen-type spirometer having an improved pneumotachometer, which has a simple structure and a low manufacturing cost and is convenient to use.

In order to achieve the above object, the present invention provides a screen-type spirometer comprising a pneumotachometer and a pressure transducer which are fluid-communicated with each other by means of a pair of flexible tubes, and comprising a flow indicating instrument which is connected to the pressure transducer by means of a conduit, the pneumotachometer including:

a hollow housing having an annularly shaped ring and a first respiratory tube integrally formed with the annularly shaped ring, the first respiratory tube capable of being inserted into a mouth of a person to be examined;

O-shaped first and second sensing units for sensing pressure of respiratory gases passing through the pneumotachometer, the O-shaped first and second sensing units being disposed within the housing, a circularly shaped screen operating as a mechanical resistance against the respiratory gases and being disposed between the first sensing unit and the second sensing unit within the housing; and a second respiratory tube cabable of being engaged with the housing and of being inserted into the mouth of the person to be exaimed.

The spirometer further comprises a blowing apparatus for drying the screen in order to remove humidity formed on the screen after using the pneumotachometer. The blowing apparatus is provided as an individual unit apart from the pneumotachometer, the pressure transducer and the flow indicating instrument, which are associated with one another.

The pneumotachometer further includes a hollow handle for allowing the person to be examined to directly use the pneumotachometer. The handle is attached to an outer surface of the annularly shaped ring.

As described above, in the screen-type spirometer according to the present invention, the improved pneumotachometer having the replaceable single screen and the handle is employed in replace of the conventional pneumotachometer having a plurality of screens. Accordingly, the screen-type spirometer has a simple structure and a low manufacturing cost, and is convenient to use.

BRIEF DESCRIPTION OF THE DRAWINGS

The above object and other characteristics and advantages of the present invention will become more apparent by describing in detail a preferred embodiment thereof with reference to the attached drawings, in which.

DETAILED DESCRIPTION OF THE INVENTION

Hereinafter, a preferred embodiment of the present invention will be explained in more detail with reference to the accompanying drawings.

Figure 1:
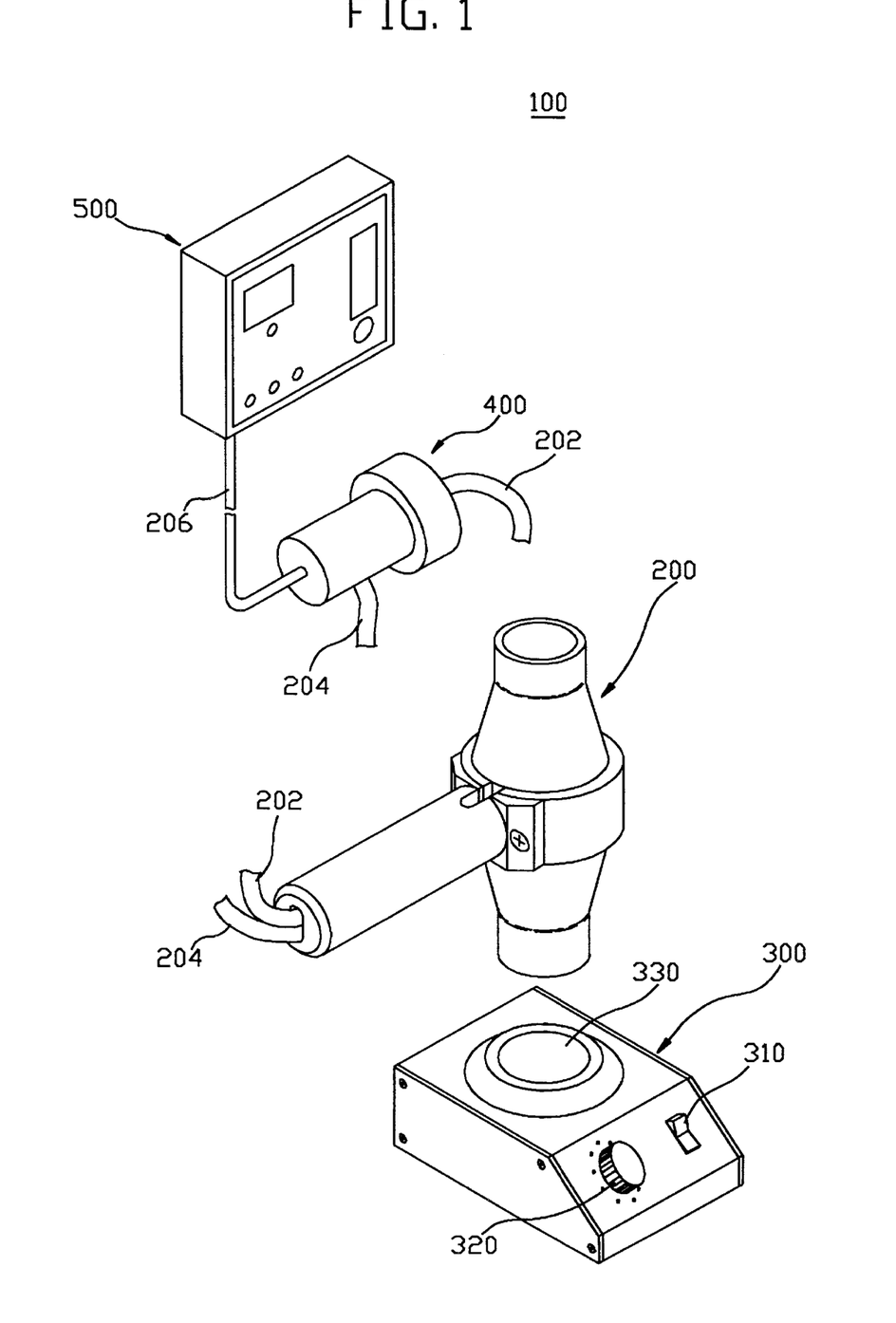
FIG. 1 illustrates schematically a screen-type spirometer according to the present invention.

FIG. 1 illustrates schematically a screen-type spirometer according to the present invention. Referring to FIG. 1, a screen-type spirometer 100 according to the preferred embodiment of the present invention mainly includes a pneumotachometer 200, a blowing apparatus 300, a pressure transducer 400 and a flow indicating instrument 500. Pneumotachometer 200 and pressure transducer 400 are fluid-communicated with each other by means of a pair of flexible tubes 202,204. Pressure transducer 400 and flow indicating instrument 500 are connected with each other by means of a conduit 206. Blowing apparatus 300 is provided as an individual unit apart from pneumotachometer 200, pressure transducer 400 and flow indicating instrument 500, which are associated with one another. Blowing apparatus 300 can be used to dry a single screen 230(referred to FIGS. 2 and 3) which is disposed within pneumotachometer 200. Blowing apparatus 300 includes a blowing fan(not shown) therein. Also, blowing apparatus 300 includes an on-off switch 310, a control switch 320 and a respiratory tube receiving portion 330.

Pressure transducer 400 senses a differential pressure created between interiors of flexible tubes 202 and 204 and converts the differential pressure into a flow measurement of the respiratory gases passing through pneumotachometer 200. The flow measurement is conducted by conduit 206 to flow indicating instrument 500. Then, flow indicating instrument 500 provides a read-out to an operator thereof on the basis of the flow measurement conducted by conduit 206 so that the operator can determine a physical condition of a person to be examined.

Figure 2:
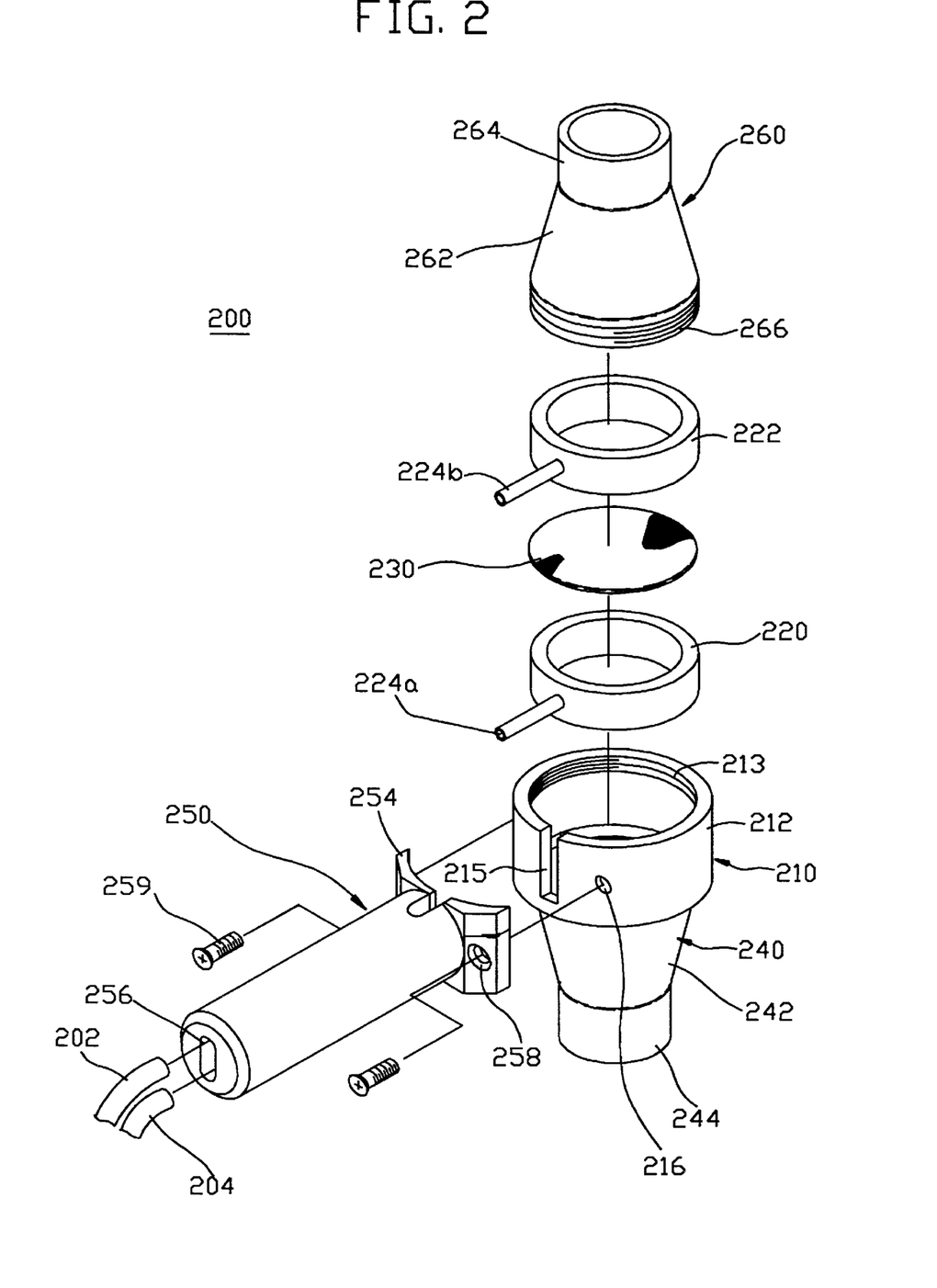
FIG. 2 is an enlarged and exploded perspective view of a pneumotachometer illustrated in FIG. 1.
Figure 3:
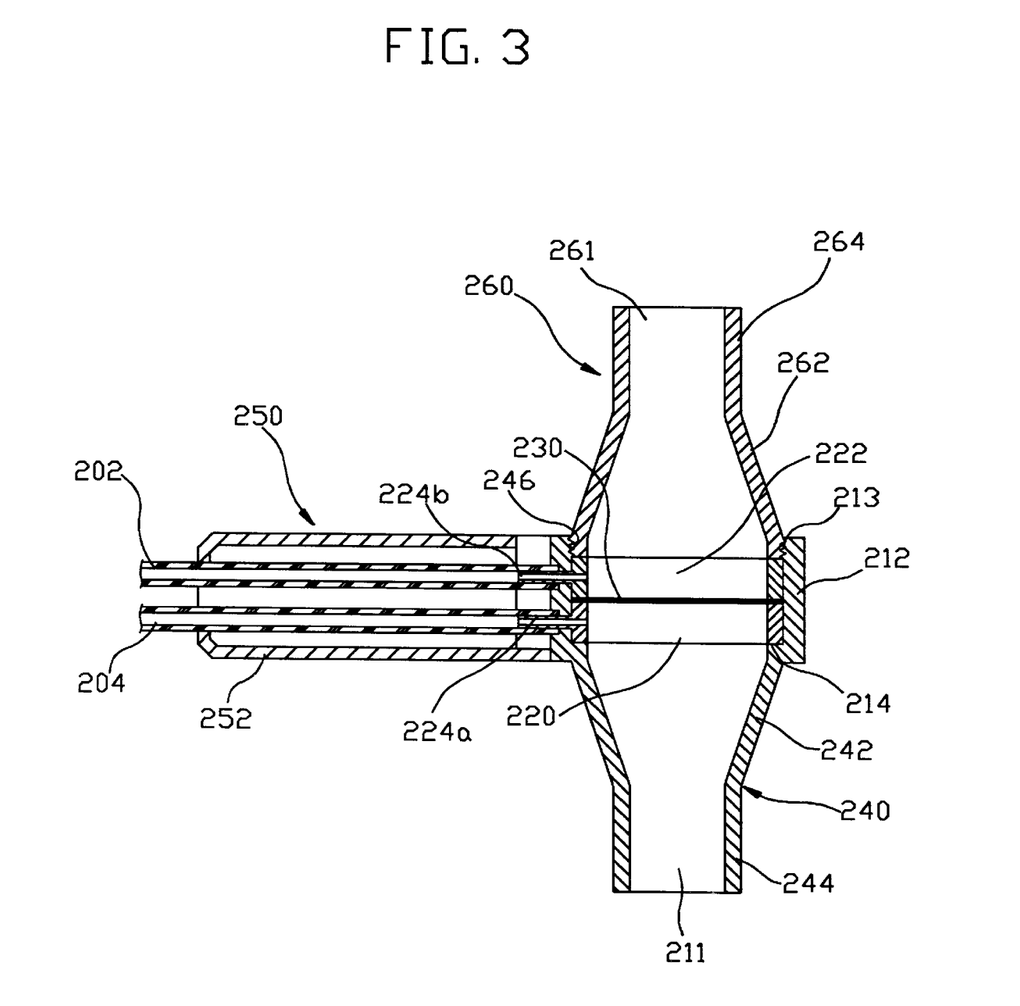
FIG. 3 is a sectional view of the pneumotachometer illustrated in FIG. 2, showing the assembled state of the overall parts constructing the pneumotachometer.

FIG. 2 is an enlarged and exploded perspective view of a pneumotachometer illustrated in FIG. 1, and FIG. 3 is a sectional view of the pneumotachometer illustrated in FIG. 2, showing the assembled state of the overall parts constructing the pneumotachometer. Referring to FIGS. 2 and 3, pneumotachometer 200 includes a hollow housing 210, an O-shaped first sensing unit 220, an O-shaped second sensing unit 222, a circularly-shaped screen 230, a hollow handle 250 and a hollow second respiratory tube 260. Housing 210 includes an annularly shaped ring 212 and a first respiratory tube 240 which is integrally formed with annularly shaped ring 212 and extends therefrom in a direction. A first passageway 211 for allowing the respiratory gases of the person to flow therethrough is formed in annularly shaped ring 212 and first respiratory tube 240 which are coaxially aligned with each other. A female threaded portion 213 is formed at an upper end of an inner surface of annularly shaped ring 212. At a position adjacent to first respiratory tube 240, a locking stage 214 extends radially inward from the inner surface of annularly shaped ring 212. When first sensing unit 220 and second sensing unit 222 are disposed within housing 210, locking stage 214 supports them and functions as a border between annularly shaped ring 212 and first respiratory tube 240.

A hose insertion groove 215 is vertically formed at an outer surface of annularly shaped ring 212. At a position adjacent to hose insertion groove 215, a pair of first screw holes 216 are formed at the outer surface of annularly shaped ring 212. A portion of first respiratory tube 240 is tapered, with the taper decreasing from a position adjacent to annularly shaped ring 212 to a free end of first respiratory tube 240. Thereby, first respiratory tube 240 has a first tapered portion 242 and a first straight portion 244. First tapered portion 242 is inclined at 10 degrees so that a fluid flow of the respiratory gases passing therethrough is stabilized. First straight portion 244 is connected to a conventional respiratory tube(not shown), which can be inserted into a mouth of the person to be examined, in order to measure the capacity of the lungs of the person.

Alternatively, first straight portion 244 can be directly inserted into the mouth of the person in order to measure the capacity of the lungs. When an inspector or a person to be examined wants to use blowing apparatus 300 in order to remove the humidity and possible dirts formed on screen 230 of pneumotachometer 200 after using pneumotachometer 200 to the person to be examined, the inspector or the person can safely insert first straight portion 244 into respiratory tube receiving portion 330(referred to FIG. 1) of blowing apparatus 300. In order to accomplish this task, first straight portion 244 has an outer diameter smaller than an inner diameter of respiratory tube receiving portion 330. First straight portion 244 has the outer diameter of between 3 and 4 cm . Preferably, first straight portion 244 has the outer diameter of 3.6 cm .

Meanwhile, handle 250 is attached to the one side surface of annularly shaped ring 212 of which hose insertion groove 215 and first screw holes 216 are formed in. When a person to be examined wants to measure the capacity of the lungs himself, the person can directly use pneumotachometer 200 under the state that he takes handle 250 of pneumotachometer 200 in his hand. Handle 250 is hollow so that flexible tubes 202,204 extending between pneumotachometer 200 and pressure transducer 400 can pass through the inside of handle 250. Handle 250 is provided with a bar-shaped grip portion 252 and an attaching portion 254 having a rounded shape corresponding to an outer shape of annularly shaped ring 212. A pair of second screw holes 258 are formed at attaching portion 254. Second screw holes 258 are corresponding to first screw holes 216 formed at the outer surface of annularly shaped ring 212. A through hole 256 for guiding flexible hoses 202,204 is formed at a distal end of handle 250. Handle 500 is attached to annularly shaped ring 212 of housing 210 by means of a pair of locking screws 259 passing through first screw holes 216 and second screw holes 258.

When pneumotachometer 200 is assembled at a one body, O-shaped first sensing unit 220, screen 230 and O-shaped second sensing unit 222 are received in housing 210 in sequence. In other words, if first sensing unit 220, screen 230 and second sensing unit 222 are inserted into housing 210 in sequence in order to assemble pneumotachometer 200 at the one body, first sensing unit 220 is laid on locking stage 214 at first and thereafter screen 230 and second sensing unit 222 are laid on first sensing unit 220 in sequence. In order to accomplish this task, first sensing unit 220, second sensing unit 222 and circularly shaped screen 230 have an outer diameter smaller than an inner diameter of annularly shaped ring 212. Prepherably, first sensing unit 220, second sensing unit 222 and screen 230 have approximately the same diameter.

First sensing unit 220 and second sensing unit 222 are made of synthetic resin according to the injection mould process. Hollow hose adapters 224a, 224b extend outward from at outer surfaces of first sensing unit 220 and second sensing unit 222, respectively. Free ends of flexible hoses 202,204 can be fitted onto hose adapters 224a,224b. When pneumotachometer 200 is fully assembled, flexible hoses 202,204 are connected to hose adapters 224a,224b at their free ends and pass through an inside of hose insertion groove 215 of annularly shaped ring 212 and the inside of handle 250, and thereafter extend toward pressure transducer 400 (referred to FIG. 1).

When pneumotachometer 200 is assembled, screen 230 is disposed between first sensing unit 220a and second sensing unit 220b and thereafter it is supported by them. At this time, screen 230 acts as a mechanical resistance against the respiratory gases. A conventional screen, which is frequently used as a particle filter during the performance of a biochemical experiment, can be employed as screen 230. Preferably, a suitable size for screen 230 has been found to be in the range of a screen having a mesh of 300 openings per inch.

Second respiratory tube 260 has a shape and a size which are the same as those of first respiratory tube 240. Second respiratory tube 260 is provided with a second tapered portion 262 and a second straight portion 264. Preferably, second tapered portion 262 is inclined at 10 degrees. When an inspector or a person to be examined wants to use blowing apparatus 300 in order to remove the humidity and dirts including microorganism formed on screen 230 of pneumotachometer 200 after using pneumotachometer 200 to the person to be examined, the inspector or the person can safely insert second straight portion 264 into respiratory tube receiving portion 330 (referred to FIG. 1) of blowing apparatus 300. In order to accomplish this task, second straight portion 264 has an outer diameter smaller than the inner diameter of respiratory tube receiving portion 330. Second straight portion 264 has the outer diameter of between 3 and 4 cm . Preferably, second straight portion 264 has the outer diameter of 3.6 cm .

A second passageway 261 for allowing the respiratory gases of the person to flow therethrough is formed in second tapered portion 262 and second straight portion 264 which are integrally formed and coaxially aligned with each other. When pneumotachometer 200 is fully assembled, second passageway 261 is fluid-communicated with first passageway 211 through screen 230. A male threaded portion 266 is formed at a free end of second tapered portion 262 of second respiratory tube 260. When pneumotachometer 200 is assembled, male threaded portion 266 is inserted into annularly shaped ring 212 of housing 210 and is engaged with female threaded portion 213. Accordingly, if screen 230 is damaged during the use of pneumotachometer 200, then the inspector can easily and conveniently replace the damaged screen 230 with a new screen 230 by turning second respiratory gase tube 260 in the counter-clockwise direction and thereafter simply separating the damaged screen 230 from housing 210.

Hereinbelow, a method of using screen-type spirometer 100 having the improved pneumotachometer 200 as described above will be briefly described.

When a sufferer from a specific disease, a patient to be undergone an operation, a general person or a sufferer from an industrial disease wants to undergo a medical health examination, he can insert first respiratory tube 240 or second respiratory tube 260 of pneumotachometer 200 into the mouth on the instructions of a doctor or an inspector. That is, the person to be examined can insert first stright portion 244 of first respiratory tube 240 or second stright portion 264 of second respiratory tube 260 into the mouth under the state that he takes handle 250 of pneumotachometer 200 in his hand.

Under this state, if the person to be examined breathes in or breathes out repeatedly, then the fluid energy of the respiratory gases is lost due to friction generated at the time that the respiratory gases pass through screen 230 acting as a mechanical resistance. As a result, differential pressure drop corresponding to the lost fluid energy is generated. At this time, the differential pressure drop is sensed by first sensing unit 220 and second sensing unit 222 and is transmitted to pressure transducer 400. Pressure transducer 400 converts the differential pressure drop transmitted form pneumotachometer 200 through flexible tubes 202,204 into a flow measurement of the respiratory gases passing through pneumotachometer 200. The flow measurement is conducted by conduit 206 to flow indicating instrument 500. Then, flow indicating instrument 500 visually indicates an output voltage corresponding to the flow measurement conducted by conduit 206 so that the doctor or the inspector can determine a physical condition of the person to be examined on the basis of the fluid flow of respiratory gases measured by pneumotachometer 200.

Figure 4:
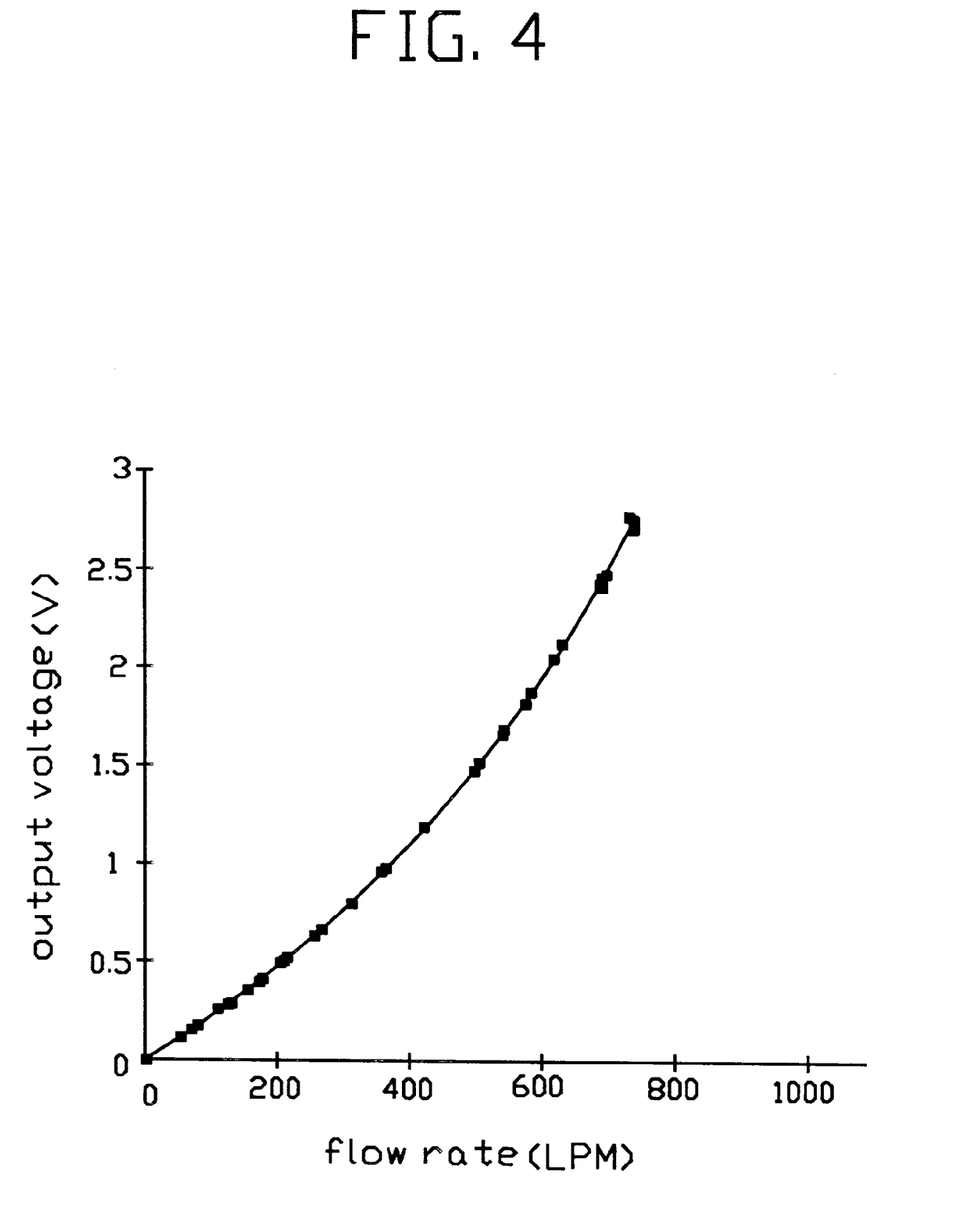
FIG. 4 is a graph showing the result of experiment in measuring a static characteristic of the pneumotachometer according to the present invention.

FIG. 4 is a graph showing the result of experiment in measuring the static characteristics of the pneumotachometer according to the present invention. Referring to FIG. 4, the static characteristics of the pneumotachometer according to the present invention is represented as a parabolic function starting at the origin. That is, according to the experiment using four screens 230, there is no difference in relation to mesh screen 230. Measurement error ranges within 5% at all measurement values. Accordingly, in the preferred embodiment according to the present invention, although the structure of the conventional pneumotachometer has been changed, it is possible to obtain an excellent static characteristic in comparison with the static characteristic obtained from the conventional pneumotach apparatus. Further, according to the experiment of measuring the dynamic response of the combination of the pneumotachometer and the pressure transducer in the screen-type spirometer according to the present invention, an excellent dynamic response is obtained, which accurately provides a continuous flow measurement.

As described above, in the screen-type spirometer according to the preferred embodiment of the present invention, the improved pneumotachometer 200 having the replaceable single screen 230 and handle 250 is employed in replace of the conventional pneumotachometer 12 having a plurality of screens 60a,60b,60c therein. Accordingly, the screen-type spirometer has a simple structure and low manufacturing cost, and is convenient to use. Further, in the screen-type spirometer 100 according to the preferred embodiment of the present invention, blowing apparatus 300 is employed in order to remove the humidity and dirts including possible microorganisms formed on screen 230 in replace of screen heater 18 for heating screens 60a,60b,60c. Accordingly, it is possible to prevent the next person to be examined from being secondarily infected. In addition, it is convenient to use screen-type spirometer 100 compared to the conventional pneumotach apparatus 10.

While the present invention has been particularly shown and described with reference to a particular embodiment thereof, it will be understood by those skilled in the art that various changes in form and details may be effected therein without departing from the spirit and scope of the invention as defined by the appended claims.

What is claimed is:

1. In a screen-type spirometer comprising a pneumotachometer and a pressure transducer which are fluid-communicated with each other by means of a pair of flexible tubes, and comprising a flow indicating instrument which is connected to the pressure transducer by means of a conduit, said pneumotachometer including:

tube integrally formed with said annularly shaped ring, said first respiratory tube capable of being inserted into a mouth of a person to be examined;

O-shaped first and second sensing units for sensing pressure of respiratory gases passing through said pneumotachometer, said O-shaped first and second sensing units being disposed within said housing;

a circularly shaped screen operating as a mechanical resistance against the respiratory gases and being disposed between said O-shaped first sensing unit and said O-shaped second sensing unit within said housing; and a second respiratory tube capable of being engaged with said housing and of being inserted into the mouth of the person to be examined, said spirometer further comprising a blowing apparatus for drying and dirt removal said screen in order to remove humidity and dirts formed on said screen after using said pneumotachometer, said blowing apparatus being provided as an individual unit apart from said pneumotachometer, said pressure transducer and said flow indicating instrument, which are associated with one another.

2. A screen-type spirometer as in claim 1, wherein said blowing apparatus includes a blowing fan, an on-off switch, a control switch and a respiratory tube receiving portion, said respiratory tube receiving portion receives said first respiratory tube or said second respiratory tube at the time that an inspector or the person to be examined lays said pneumotachometer on said blowing apparatus in order to remove at the same time both the humidity and dirts formed on said screen after using said pneumotachometer.

3. The screen-type spirometer as in claim 1, wherein said pneumotachometer further includes a hollow handle for allowing the person to be examined to directly use said pneumotachometer, said handle is attached to an outer surface of said annularly shaped ring.

4. The screen-type spirometer as in claim 2, wherein said handle is provided with a bar-shaped grip portion and an attaching portion having a rounded shape corresponding to an outer shape of said annularly shaped ring, in which a pair of second screw holes are formed at said attaching portion, said second screw holes are corresponding to a pair of first screw holes formed at the outer surface of said annularly shaped ring, a through hole for guiding said flexible hoses is formed at a distal end of said handle, said handle is attached to said annularly shaped ring of said housing by means of a pair of locking screws passing through said first screw holes and said second screw holes.

5. The screen-type spirometer as in claim 1, wherein a first passageway for allowing the respiratory gases of the person to flow therethrough is formed in said annularly shaped ring and said first respiratory tube which are coaxially aligned with each other, said annularly shaped ring has a female threaded portion which is formed at an upper end of an inner surface thereof and a locking stage extending radially inward from the inner surface thereof at a position adjacent to said first respiratory tube, a hose insertion groove is vertically formed at an outer surface of said annularly shaped ring, and a pair of first screw holes are formed at the outer surface of said annularly shaped ring at a position adjacent to said hose insertion groove.

6. The screen-type spirometer as in claim 5, wherein said first respiratory tube has a first tapered portion and a first straight portion, said first tapered portion is inclined at 10 degrees so that a fluid flow of the respiratory gases passing therethrough is stabilized, said first straight portion has an outer diameter of between 3 and 4 cm .

7. The screen-type spirometer as in claim 1, wherein said O-shaped first and second sensing units are made of synthetic resin according to the injection mould process and have an outer diameter smaller than an inner diameter of said annularly shaped ring, hollow hose adapters extend outward from at outer surfaces of said O-shaped first and second sensing units, respectively, and free ends of said flexible hoses can be fitted onto said hose adapters.

8. The screen-type spirometer as in claim 1, wherein said screen comprises a screen having a mesh of 300 openings per inch.

9. The screen-type spirometer as in claim 1, wherein said second respiratory tube has a second tapered portion and a second straight portion, said second tapered portion is inclined at 10 degrees so that a fluid flow of the respiratory gases passing therethrough is stabilized, said second straight portion has an outer diameter of between 3 and 4 cm .

10. The screen-type spirometer as in claim 9, wherein a second passageway for allowing the respiratory gases of the person to flow therethrough is formed in said second tapered portion and said second straight portion which are coaxially aligned with each other, said second tapered portion has a male threaded portion which is formed at a free end thereof, said male threaded portion is engaged with said female threaded portion which is formed at the upper end of the inner surface of said annularly shaped ring while said pneumotachometer is assembled.

11. In a screen-type spirometer comprising a pneumotachometer and a pressure transducer which are fluid-communicated with each other by means of a pair of flexible tubes, and comprising a flow indicating instrument which is connected to the pressure transducer by means of a conduit, said pneumotachometer including:

a hollow housing having an annularly shaped ring and a first respiratory tube integrally formed with said annularly shaped ring, said first respiratory tube capable of being inserted into a mouth of a person to be examined;

O-shaped first and second sensing units for sensing pressure of respiratory gases passing through said pneumotachometer, said O-shaped first and second sensing units being disposed within said housing and being made of synthetic resin according to the injection mould process, said O-shaped first and second sensing units having an outer diameter smaller than an inner diameter of said annularly shaped ring, in which hollow hose adapters extend outward from at outer surfaces of said O-shaped first and second sensing units, respectively, and free ends of said flexible hoses can be fitted onto said hose adapters;

a circularly shaped screen operating as a mechanical resistance against the respiratory gases and being disposed between said O-shaped first sensing unit and said O-shaped second sensing unit within said housing;

a second respiratory tube capable of being engaged with said housing and of being inserted into the mouth of the person to be examined; and a hollow handle for allowing the person to be examined to directly use said pneumotachometer, said handle being attached to an outer surface of said annularly shaped ring, said handle being provided with a bar-shaped grip portion and an attaching portion having a rounded shape corresponding to an outer shape of said annularly shaped ring, in which a pair of second screw holes are formed at said attaching portion, said second screw holes are corresponding to a pair of first screw holes formed at the outer surface of said annularly shaped ring, a through hole for guiding said flexible hoses is formed at a distal end of said handle, said handle is attached to said annularly shaped ring of said housing by means of a pair of locking screws passing through said first screw holes and said second screw holes said spirometer further comprising a blowing apparatus for drying said screen in order to remove humidity and dirts including possible microorganisms formed on said screen after using said pneumotachometer said blowing apparatus being provided as an individual unit apart from said pneumotachometer, said pressure transducer and said flow indicating instrument, which are associated with one another.

12. The screen-type spirometer as in claim 11, wherein said blowing apparatus includes a blowing fan, an on-off switch, a control switch and a respiratory tube receiving portion, said respiratory tube receiving portion receives said first respiratory tube or said second respiratory tube at the time that an inspector or the person to be examined lays said pneumotachometer on said blowing apparatus in order to remove the humidity and dirts formed on said screen after using said pneumotachometer.

13. The screen-type spirometer as in claim 11, wherein a first passageway for allowing the respiratory gases of the person to flow therethrough is formed in said annularly shaped ring and said first respiratory tube which are coaxially aligned with each other, said annularly shaped ring has a female threaded portion which is formed at an upper end of an inner surface thereof and a locking stage extending radially inward from the inner surface thereof at a position adjacent to said first respiratory tube, and a hose insertion groove is vertically formed at an outer surface of said annularly shaped ring.

14. The screen-type spirometer as in claim 11, wherein said first respiratory tube has a first tapered portion and a first straight portion, said first tapered portion is inclined at 10 degrees so that a fluid flow of the respiratory gases passing therethrough is stabilized, said first straight portion has an outer diameter of between 3 and 4 cm.

15. The screen-type spirometer as in claim 11, wherein said screen comprises a screen having a mesh of 300 openings per inch.

16. The screen-type spirometer as in claim 11, wherein said second respiratory tube has a second tapered portion and a second straight portion, said second tapered portion is inclined at 10 degrees so that a fluid flow of the respiratory gases passing therethrough is stabilized, said second straight portion has an outer diameter of between 3 and 4 cm.

17. The screen-type spirometer as in claim 11, wherein a second passageway for allowing the respiratory gases of the person to flow therethrough is formed in said second tapered portion and said second straight portion which are coaxially aligned with each other, said second tapered portion has a male threaded portion which is formed at a free end thereof, said male threaded portion is engaged with said female threaded portion which is formed at the upper end of the inner surface of said annularly shaped ring while said pneumotachometer is assembled.

* * * * *